(12) United States Patent
Khoury

(10) Patent No.: US 9,017,275 B2
(45) Date of Patent: Apr. 28, 2015

(54) DISTAL PERFUSION SHEATH

(75) Inventor: Michael D. Khoury, St. George, UT (US)

(73) Assignee: Khoury Medical Devices, LLC, Saint George, UT (US)

( * ) Notice: Subject to any disclaimer, the term of this patent is extended or adjusted under 35 U.S.C. 154(b) by 469 days.

(21) Appl. No.: 13/548,458

(22) Filed: Jul. 13, 2012

(65) Prior Publication Data

US 2013/0018297 A1  Jan. 17, 2013

Related U.S. Application Data

(60) Provisional application No. 61/507,492, filed on Jul. 13, 2011, provisional application No. 61/510,786, filed on Jul. 22, 2011.

(51) Int. Cl.
*A61M 19/00* (2006.01)
*A61B 1/00* (2006.01)
*A61F 2/06* (2013.01)

(52) U.S. Cl.
CPC ............... *A61B 1/00135* (2013.01); *A61F 2/06* (2013.01); *A61F 2002/061* (2013.01); *A61F 2002/065* (2013.01)

(58) Field of Classification Search
CPC .......... A61F 2002/061; A61M 27/002; A61M 25/0026; A61M 25/0028; A61M 2025/004
USPC ........................ 604/8, 9, 264, 507, 167.3, 539
See application file for complete search history.

(56) References Cited

U.S. PATENT DOCUMENTS

| | | |
|---|---|---|
| 4,540,402 A | 9/1985 | Aigner |
| 5,284,473 A | 2/1994 | Calabria |
| 5,876,367 A | 3/1999 | Kaganov et al. |
| 6,161,547 A | 12/2000 | Barbut |
| 6,508,777 B1 | 1/2003 | Macoviak et al. |
| 6,579,311 B1 | 6/2003 | Makower |
| 2013/0018297 A1 | 1/2013 | Khoury |

*Primary Examiner* — Leslie Deak
(74) *Attorney, Agent, or Firm* — Blue Filament Law PLLC; Avery N. Goldstein

(57) ABSTRACT

A distal perfusion sheath (DPS) is provided for cases where blood perfusion is needed for downstream arteries (distal) to the insertion point of the DPS within the target artery. The ability to provide distal perfusion with the DPS allows the DPS to be positioned in the target artery for long periods without causing lack of blood flow (ischemia) to an extremity that the target artery supplies. In embodiments, the DPS can still be used for surgical arterial access while allowing blood flow downstream. In addition, embodiments of the DPS configured with longer perfusion shunts can allow a contra-lateral extremity downstream to a large DPS to have blood flow while the sheath is in place.

20 Claims, 8 Drawing Sheets

DISTAL PERFUSION SHEATH

CROSS-REFERENCE TO RELATED APPLICATIONS

This application is a non-provisional application that claims priority benefit of U.S. Provisional Application Ser. No. 61/507,492, filed Jul. 13, 2011 and U.S. Provisional Application Ser. No. 61/510,786, filed Jul. 22, 2011; the contents of which are hereby incorporated by reference.

FIELD OF THE INVENTION

The present invention in general relates to arterial sheaths and method for surgical deployment thereof, and in particular to a vascular sheath that facilitates blood perfusion to a distal artery thereby preventing ischemia to the extremity the artery supplies.

BACKGROUND OF THE INVENTION

As endovascular procedures become more complicated, the procedures often take longer to perform and often require larger sheaths to be in a patient's arteries for extended periods of time. However, larger surgical sheaths impair blood flow to a distal extremity and can cause injury to the nerves and muscles. In addition, after prolonged lack of blood flow (ischemia) the extremity is at risk for re-perfusion injury once the sheath is removed that can increase muscle compartment pressures (compartment syndrome), which can result in muscle necrosis and amputation.

Thus, there exists a need for a vascular surgical sheath that allows continued blood flow past the insertion point of the sheath, while the sheath is in place, to an extremity downstream to the sheath. There further exists a need for a process for usage of such a sheath to inhibit compartment syndrome.

SUMMARY OF THE INVENTION

An inventive distal perfusion sheath (DPS) is provided for cases where blood perfusion is needed for downstream arteries (distal) to the insertion point of the DPS within the target artery. The ability to provide distal perfusion with the DPS allows the DPS to be positioned in the target artery for long periods without causing lack of blood flow (ischemia) to an extremity that the target artery supplies. In specific embodiments, the DPS is used for surgical arterial access while allowing blood flow downstream. In addition, embodiments of the DPS configured with longer perfusion shunts can allow a contra-lateral extremity downstream to a large DPS to have blood flow while the sheath is in place.

Embodiments of the DPS have at least 2 lumens, one for arterial access and an outer expandable lumen for blood flow into the perfusion shunt. The outer lumen that feeds blood or other fluids is expanded once the sheath is in the artery. The outer lumen is expanded by injecting fluid into scaffolding that expands the lumen. The outer lumen allows arterial blood to flow through a perfusion shunt that is attached to the external distal end of the sheath. The end of the perfusion shunt may then be inserted into an artery downstream (distal) to the sheath providing blood flow to the extremity. The insertion of the perfusion shunt can be accomplished by making a small incision (arteriotomy) in the artery just below the sheath. The end of the perfusion shunt is then placed into the artery and secured with a vessel loop. The insertion of the perfusion shunt into a distal portion of the artery allows continued blood flow into the artery downstream from the sheath. At the end of the surgical procedure the perfusion shunt is removed and the incision in the distal artery is repaired.

In an embodiment, in cases that require large specialized sheaths, downstream flow can be provided by placing a distal perfusion sheath in the opposite extremity artery. The distal perfusion sheath can be small enough to allow continued blood flow to the downstream extremity. The perfusion shunt can then be inserted into the artery just below the opposite sheath to provide blood flow to the opposite extremity.

DESCRIPTION OF THE PREFERRED EMBODIMENTS

Figure 1A:
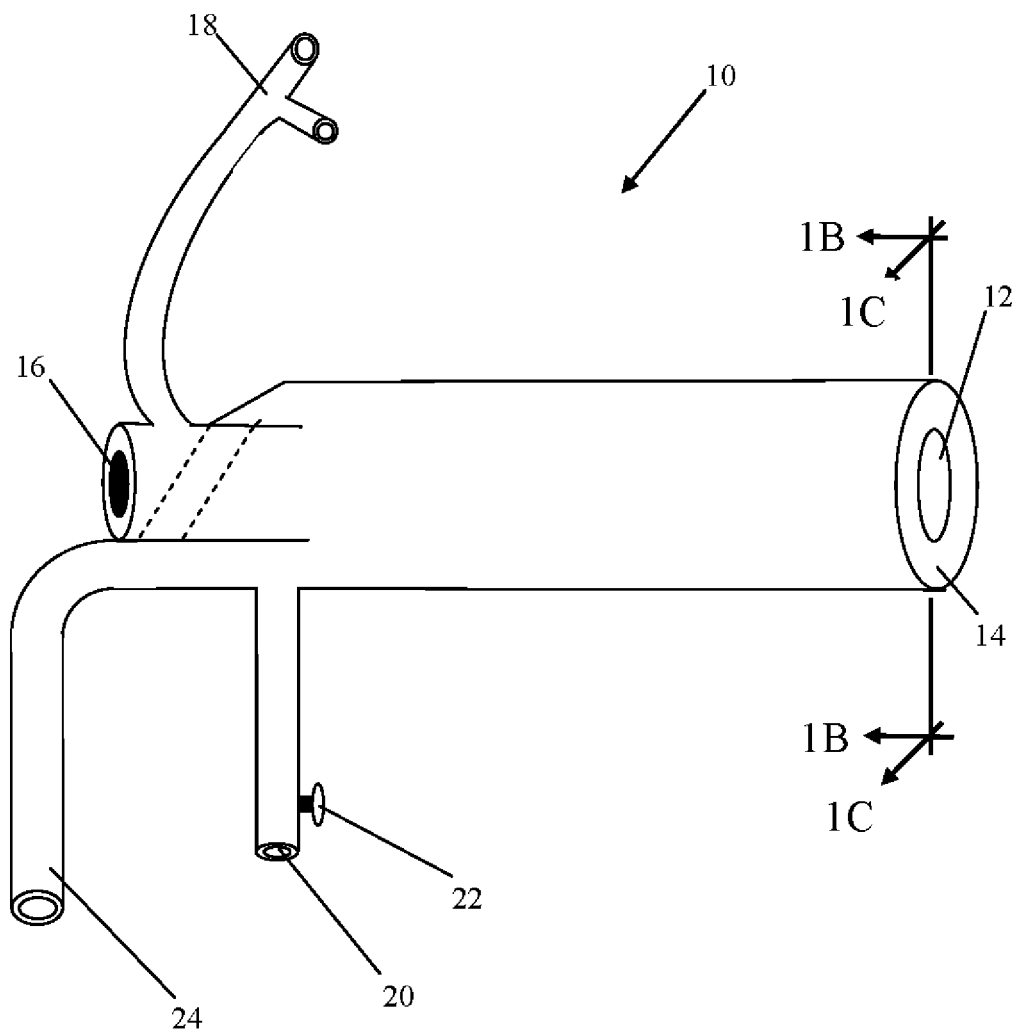
FIG. 1A is a perspective view of an inventive distal perfusion sheath (DPS) device.
Figure 1B:
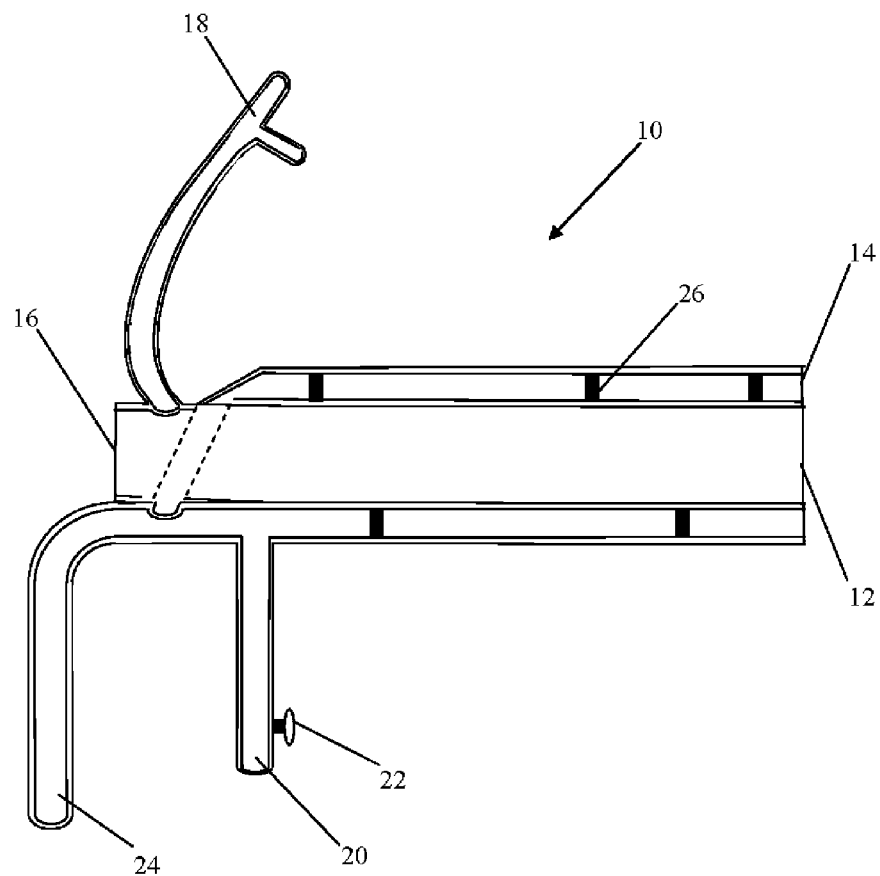
FIG. 1B is a longitudinal cross-sectional view of the device of FIG. 1A along line 1B-1B.
Figure 1C:
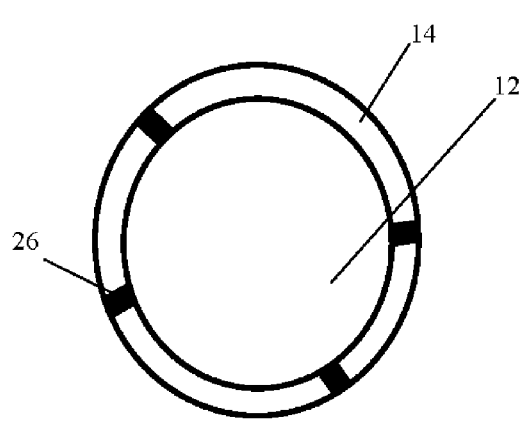
FIG. 1C is a cross-sectional view of the device of FIG. 1A along line 1C-1C.
Figure 1D:
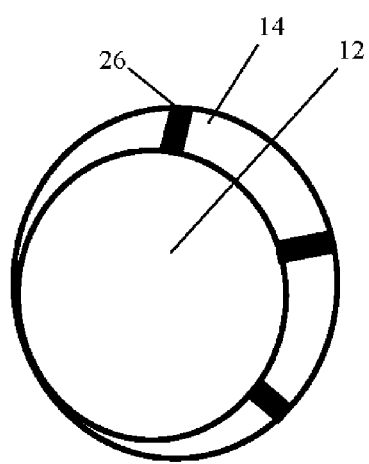
FIG. 1D is a cross-sectional view of an alternative device of FIG. 1A along line 1C-1C where the inner lumen for arterial access and an outer expandable lumen are eccentric.

An inventive distal perfusion sheath (DPS) provides blood perfusion to the artery downstream (distal) to the insertion point within the artery. The ability to provide distal perfusion with the DPS allows the DPS to be positioned in the artery for long periods without causing lack of blood flow (ischemia) to an extremity that the artery supplies. In embodiments, the DPS can still be used for surgical arterial access while allowing blood flow downstream. In addition, embodiments of the DPS configured with longer perfusion shunts can allow a contra-lateral extremity downstream to a large DPS to have blood flow while the sheath is in place.

Embodiments of the DPS have at least 2 lumens, one for arterial access and an outer expandable lumen for blood flow into the perfusion shunt. The outer lumen that feeds blood or other fluids is expanded once the sheath is in the artery. The outer lumen is expanded by injecting fluid into scaffolding that expands the lumen. The outer lumen allows arterial blood to flow through a perfusion shunt that is attached to the external distal end of the sheath. The end of the perfusion shunt may then be inserted into an artery downstream (distal) to the sheath providing blood flow to the extremity. The insertion of the perfusion shunt can be accomplished by making a small incision (arteriotomy) in the artery just below the sheath. The end of the perfusion shunt is then placed into the artery and secured with a vessel loop. The insertion of the perfusion shunt into a distal portion of the artery allows continued blood flow into the artery downstream from the sheath. At the end of the surgical procedure the perfusion shunt is removed and the incision in the distal artery is repaired.

In a specific embodiment, in cases that require large specialized sheaths, downstream flow can be provided by placing a distal perfusion sheath in the opposite extremity artery. The distal perfusion sheath can be small enough to allow continued blood flow to the downstream extremity. The perfusion shunt can then be inserted into the artery just below the opposite sheath to provide blood flow to the opposite extremity. The inventive sheath is readily constructed with biocompatible polyurethane materials, with possible metal, or Nitinol reinforcement. It is appreciated that an inventive sheath optionally and readily incorporates substances such as radio opaque marking compounds on the catheter for accurate positioning such as barium sulfate; slip agents for smooth artery entry such as hydrophilic gels sold under that tradename GLIDEX®; anticoagulants such as heparin; sustained release drugs such as antibiotics and plaque formation inhibitors; and combinations thereof.

Referring now to FIGS. 1 and 2, an inventive distal perfusion sheath (DPS) is depicted generally at 10. The DPS 10 includes an inner lumen 12 for arterial access and an outer expandable lumen 14 for blood flow into the perfusion shunt 24. The outer lumen 14 is expanded following the insertion of the DPS 10 into an artery V (FIGS. 2A, 2C, and 2D) by injecting fluid through port 20 with control valve 22 to inflate scaffolds 26 as depicted in FIGS. 1B, 1C, 1D, and 2D. FIG. 1C is a cross-sectional view of the device of FIG. 1A along line 1C-1C where the inner lumen 12 for arterial access and an outer expandable lumen 14 are concentric with the scaffolds 26 evenly distributed along the circumference of the inner lumen 12. FIG. 1D is a cross-sectional view of the device of FIG. 1A along line 1C-1C where the inner lumen 12 for arterial access and an outer expandable lumen 14 are not concentric with the scaffolds 26 positioned primarily to one side. The scaffolds 26, which do not obstruct blood flow, expand the outer lumen 14 until the outer dimensions of outer lumen 14 contact the inner diameter of the artery V, regardless of whether a concentric or eccentric embodiment is in usage. Hemostatic port 16 controls blood flow in the inner lumen 12, and allows for insertion of a catheter, guide wire, camera, or other surgical device into the artery V. Flush port 18 controls fluids in the inner lumen 12. While the inner lumen 12 and outer lumen 14 are depicted as being concentric in FIG. 1C, it is appreciated that asymmetric placement or expansion of scaffolds 26 affords an eccentric arrangement of inner lumen 12 and outer lumen 14, as shown in FIG. 1D, where like numeral have the meanings previously ascribed thereto.

Figure 2A:
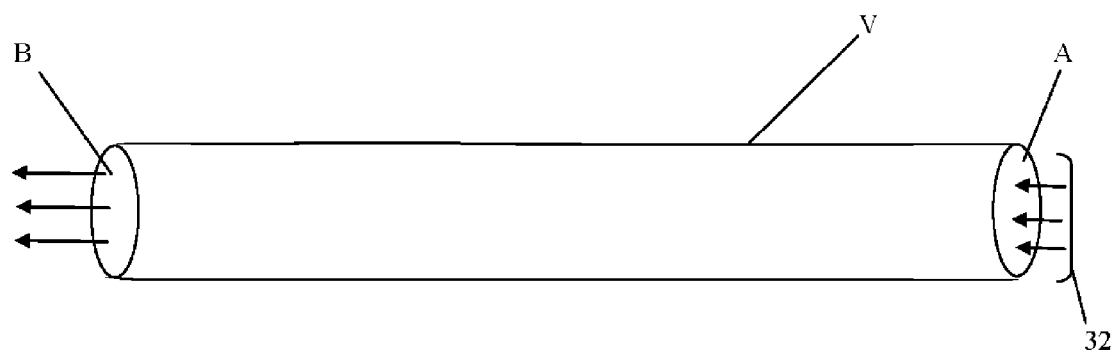
FIG. 2A is a perspective view of an artery prior to the insertion of a sheath.
Figure 2B:
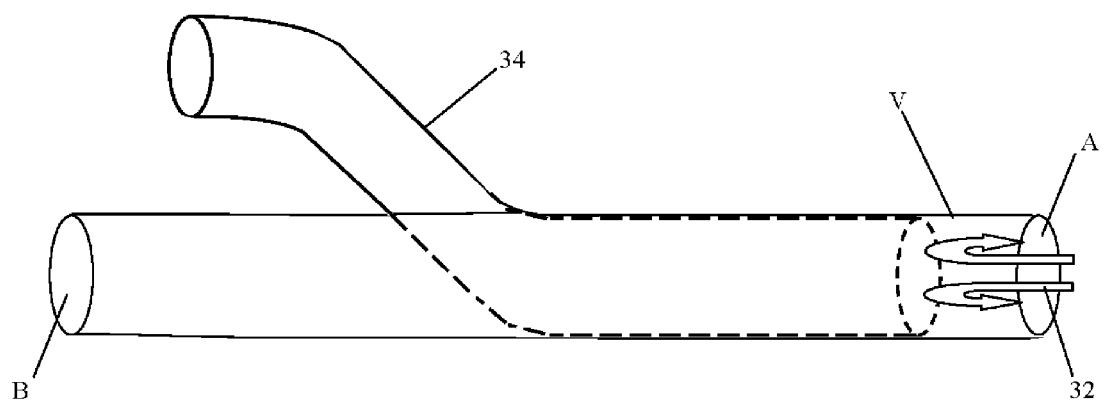
FIG. 2B is a perspective view of an artery with a conventional prior art sheath inserted, and the resultant impaired blood flow in the artery.
Figure 2C:
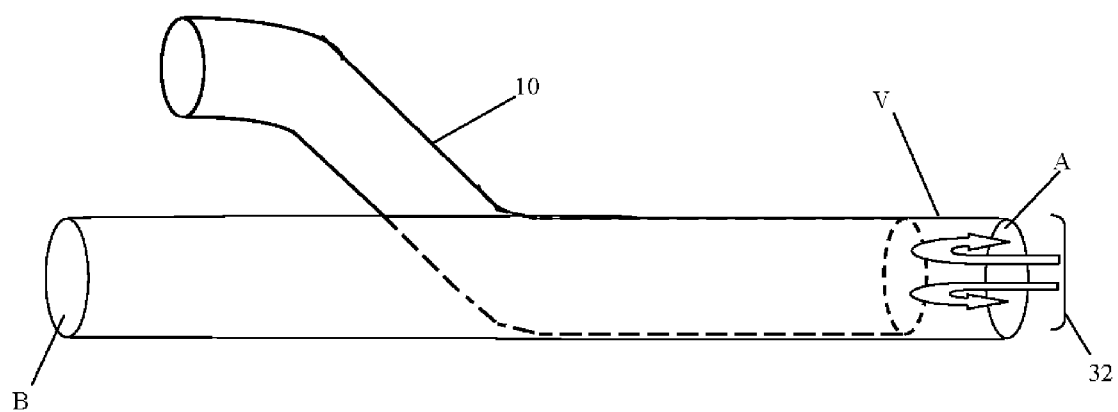
FIG. 2C is a perspective view of an artery with the inventive distal perfusion sheath inserted, prior to inflation of channels for distal perfusion.
Figure 2D:
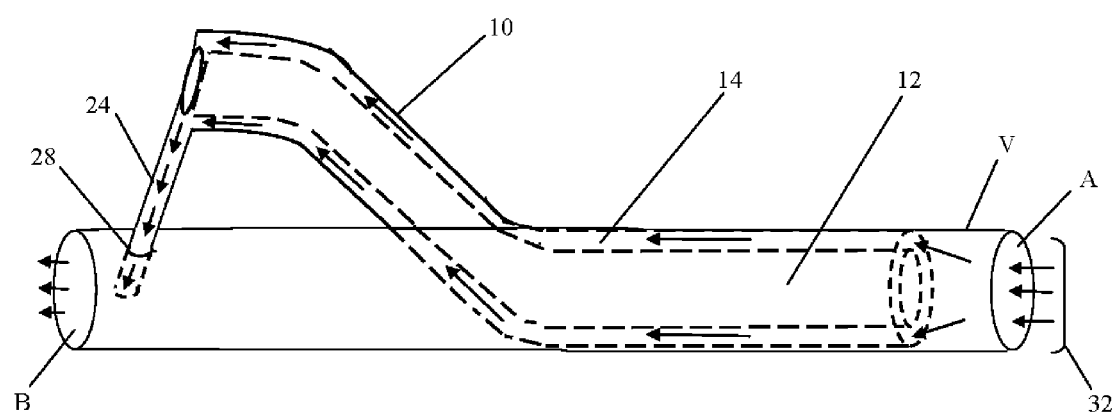
FIG. 2D is a perspective view of an artery with the inventive distal perfusion sheath inserted, and the distal perfusion channels inflated to allow blood flow past the sheath.

FIG. 2A depicts an artery V prior to the insertion of a sheath. Prior to the insertion of a sheath blood flow 32 is relatively unimpeded from proximal end A to distal end B. In FIG. 2B, a conventional sheath 34 is inserted in artery V with a resultant impairment of blood or fluid flow 32 from proximal end A to distal end B. In a similar manner in FIG. 2C, an embodiment of the DPS 10, with the perfusion shunt 24 not deployed, is inserted into artery V with an impairment of blood flow 32 from proximal end A to distal end B. However, as shown in FIG. 2D with the opening of the outer lumen 14 blood flow 32 commences from proximal end A to distal end B through perfusion shunt 24, the perfusion shunt 24 inserted into the distal portion of artery V through incision 28. Thus as shown in FIG. 2D with the DPS 10 fully deployed (outer lumen 14 open) and perfusion shunt 24 inserted in the distal portion of artery V, blood flow is rerouted beyond the DPS 10.

FIGS. 3 and 4A-4D illustrate an embodiment of a distal perfusion sheath (DPS) 40 employing multiple guidewires (42a, 42b, 42c) for implementations where simultaneous guidewire access to multiple target arteries is required without disrupting blood flow to a distal bodily extremity that the artery supplies. An engagement system (44a, 44b, 44c) independently secures the one or more guidewires within the sheath of the DPS 40 to maintain the separate positions of the guidewires. The engagement system (44a, 44b, 44c) is a series of wire-lock engagement points (44a, 44b, 44c) positioned along for example, the circumference of an inventive sheath. Selection of a guidewire is made with a rotating hub 46 with a hemostatic port 16 at the center.

In operation, the rotation of the hub 46 at the distal end of the DPS allows the slit 48 of the hemostatic port 16 to line up with a desired wire-lock (44a, 44b, 44c) of the engagement system to allow the guidewire to be positioned in and out of the wire-lock. When the locked guidewire is to be used in the main sheath lumen or inner lumen 12 of the DPS 40, the hub 46 is rotated to line up the valve-slit with the guidewire in the wire-lock. The lock is opened releasing the guidewire which is then moved through the valve-slit to the center hub of the hemostatic valve and then used in a conventional manner in a target artery. Following the usage of the unlocked guidewire, the guidewire is returned through the valve-slit to the wire-lock to be reengaged. The wire-lock when closed secures the guidewire in place preventing it from being dislodged while the main inner lumen 12 of the sheath is used with other guidewires. The hub 46 may then be rotated to line up the valve-slit 48 with another wire-lock to access a different guidewire for serving the same or different target artery.

Figure 3:
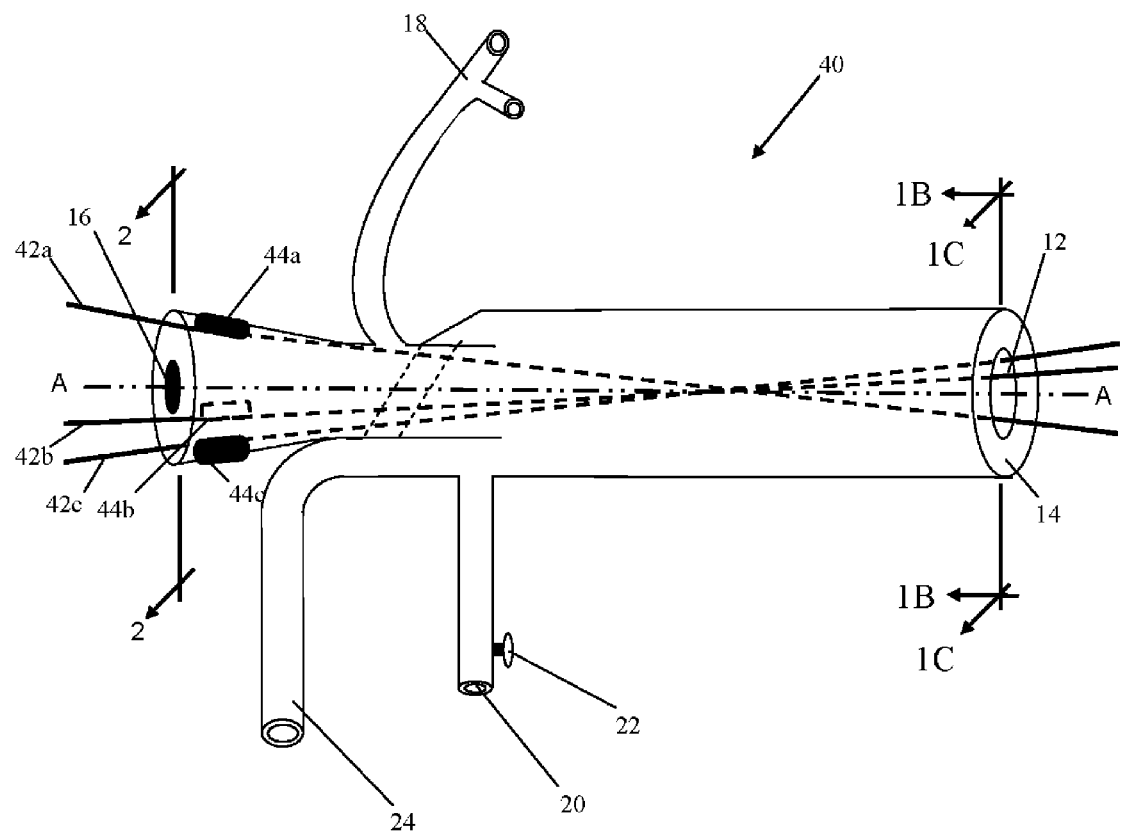
FIG. 3 is a perspective view of an embodiment of an inventive distal perfusion sheath configured with multiple guidewires in the sheath.
Figures 4A, 4B:
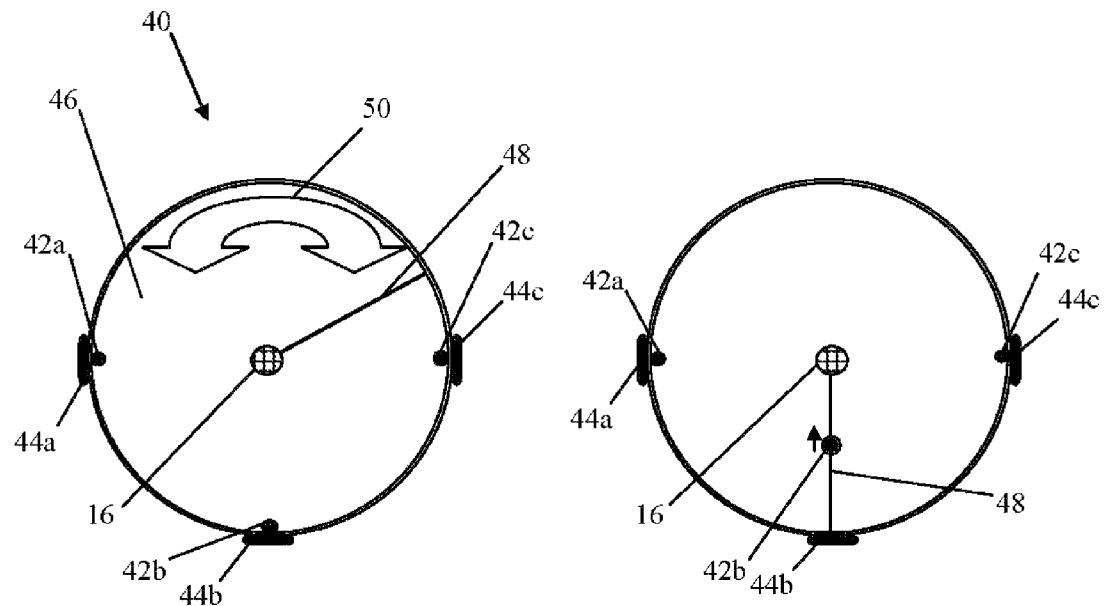
FIGS. 4A-4D are a series of cross-sectional views of the device of FIG. 3 along line 2-2 illustrating the unlocking and repositioning of a guidewire from amongst the three guidewires in the sheath.
Figures 4C, 4D:
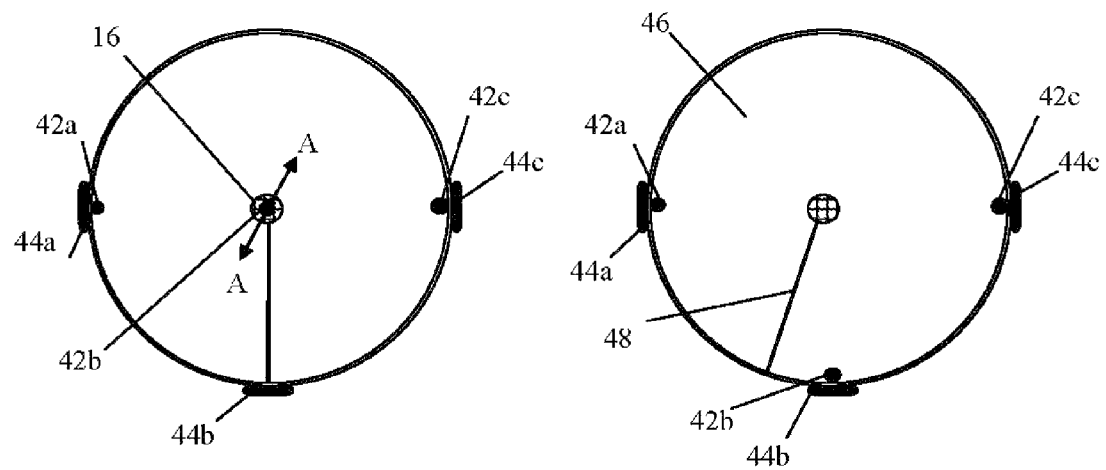

FIGS. 4A-4D are a series of cross-sectional views of the DPS device 40 of FIG. 3 along line 2-2 illustrating the unlocking and repositioning of the guidewire 42b. In FIG. 2A, all three of the guidewires (42a, 42b, 42c) are secured or locked to the engagement system (44a, 44b, 44c). In FIG. 2B, the rotating hub 46, which is free to rotate either clockwise or counter-clockwise as indicated by the bidirectional arrow 50, is rotated to position the slit 48 to line up with engagement 44b, and the guidewire 42b is unlocked from engagement 44b and moved inward toward the hemostatic valve seal port 16 in the center of the rotating hub 46. In FIG. 2C, the guidewire 42b is now positioned within the hemostatic valve seal port 16, and the guidewire is now free to move back and forth, or be twisted, along the longitudinal axis A-A of DPS device 40. In FIG. 2D, the guidewire 42b is returned to engagement 44b, and locked in place. The rotating hub 46 and corresponding slit 48 are now free to be rotated to another of the engagement 44a or 44c for using guidewires 42a or 42c, respectively.

The foregoing description is illustrative of particular embodiments of the invention, but is not meant to be a limitation upon the practice thereof. The following claims, including all equivalents thereof, are intended to define the scope of the invention.

The invention claimed is:
1. A sheath for insertion into an artery, said sheath comprising:
   an inner lumen;
   an outer lumen surroundingly attached to said inner lumen with expandable scaffolds therebetween; and
   a perfusion shunt in fluid communication with said outer lumen, said perfusion shunt configured for insertion into a distal portion of the artery beyond said sheath to pro- vide blood flow from a proximal portion of the artery prior to said inserted sheath to the distal portion of the artery.

2. The sheath of claim 1 wherein said inner lumen and said outer lumen are concentric.

3. The sheath of claim 1 wherein said inner lumen and said outer lumen are eccentric.

4. The sheath of claim 1 wherein said inner lumen is configured for the insertion of at least one of: a catheter, guide wire, camera, or other device into said artery.

5. The sheath of claim 4 wherein said flush port controls fluids in said inner lumen.

6. The sheath of claim 1 wherein said inner lumen further comprises a hemostatic port and a flush port.

7. The sheath of claim 6 wherein said hemostatic port controls blood flow in said inner lumen, and is configured for insertion of a catheter, guide wire, camera, or other device into the artery.

8. The sheath of claim 1 wherein said scaffolds are expanded by injecting fluids into a port connected to said outer lumen.

9. The sheath of claim 8 wherein said biocompatible polyurethane materials are reinforced with metal.

10. The sheath of claim 8 wherein said biocompatible polyurethane materials are reinforced with Nitonal.

11. The sheath of claim 1 wherein said sheath is constructed with biocompatible polyurethane materials.

12. A method of using the sheath of claim 1, the method comprising:
inserting said sheath in a patient artery;
inserting said perfusion shunt in said distal portion of said artery with a small incision (arteriotomy) in said distal portion of said artery just below said sheath;
securing said perfusion shunt to said distal portion of said artery with a vessel loop; and
inflating said scaffolds of said outer lumen.

13. A sheath for insertion into an artery, said sheath comprising:
an inner lumen with a proximal end configured for insertion into said artery, and a distal end that tapers outward;
an outer lumen concentrically attached to said inner lumen with expandable scaffolds;
a perfusion shunt in fluid communication with said outer lumen, said perfusion shunt configured for insertion into a distal portion of said artery beyond said sheath to provide blood flow from a proximal portion of said artery prior to said inserted sheath to said distal portion of said artery;
a plurality of guidewires within said inner lumen;
an engagement system with a series of wire-lock engagement points affixed to said distal end for individually engaging each of said plurality of guidewires; and
a rotatable hub at said distal end centered on a longitudinal axis of said sheath configured with a hemostatic valve at said center and a slit extending from said hemostatic valve to an outer edge of said hub.

14. The sheath of claim 13 wherein each of said plurality of guidewires is individually adjustable.

15. The sheath of claim 14 wherein in the event said guidewire is positioned in said hemostatic valve, said guidewire is free to move back and forth, or be twisted, along a longitudinal axis of said sheath.

16. The sheath of claim 13 wherein a guidewire from said plurality of guidewires is adjustable when said slit is aligned with an engagement point corresponding to said guidewire, and the engagement point is unlocked to provide movement of said guidewire to said hemostatic valve via said slit.

17. The sheath of claim 13 wherein said plurality of guidewires when engaged in said series of wire-lock engagement points are prevented from being dislodged when one guidewire from one of said plurality of guidewires is being used in said sheath.

18. The sheath of claim 13 wherein said engagement system secures said plurality of guidewires in independent positions in multiple target arteries.

19. The sheath of claim 13 wherein said sheath is constructed with biocompatible polyurethane materials.

20. The sheath of claim 19 wherein said biocompatible polyurethane materials are reinforced.

* * * * *